United States Patent [19]

Bockman et al.

[11] Patent Number: 4,686,104

[45] Date of Patent: Aug. 11, 1987

[54] METHODS OF TREATING BONE DISORDERS

[75] Inventors: Richard S. Bockman; Raymond P. Warrell, Jr., both of New York, N.Y.

[73] Assignee: Sloan-Kettering Institute for Cancer Research, New York, N.Y.

[21] Appl. No.: 853,144

[22] Filed: Apr. 22, 1986

Related U.S. Application Data

[63] Continuation-in-part of Ser. No. 729,057, Apr. 30, 1985.

[51] Int. Cl.⁴ .................. A61K 33/24; A61K 31/28
[52] U.S. Cl. .................................. 424/131; 514/492
[58] Field of Search ..................... 424/131; 514/492

[56] References Cited

U.S. PATENT DOCUMENTS

| | | | |
|---|---|---|---|
| 4,004,003 | 1/1977 | Babcock et al. | 514/167 |
| 4,302,446 | 11/1981 | Kaplan et al. | 424/131 |
| 4,529,593 | 7/1985 | Warrell et al. | 424/147 |
| 4,596,710 | 6/1986 | Collery | 424/131 |

OTHER PUBLICATIONS

Warrell, et al., J. Clin. Invest. 73: 1487–1490 (May 1984).
Leyland–Jones, et al., Cancer Treat. Resp. 67(10): 941–942 (Oct. 1983).
Kukla, et al., Clin. Res. 31(4): 739A (1983).
Warrell, et al., Cancer 51(11): 1982–1987 (Jun., 1983).
Blachley, et al., Ann. Int. Med. 95: 628–632 (1981).

*Primary Examiner*—Leonard Schenkman
*Attorney, Agent, or Firm*—John P. White

[57] ABSTRACT

Metal-containing compounds have been found to decrease calcium resorption from bone. These compounds, when administered to patients who are suffering from diseases characterized by accelerated bone resorption, impede the flow of bone calcium into the blood and increase the calcium content of bone tissue.

31 Claims, No Drawings

METHODS OF TREATING BONE DISORDERS

FIELD OF THE INVENTION

This application is a continuation in part of Ser. No. 729,057, filed Apr. 30, 1985.

This invention relates to a method for treatment of disorders associated with bone resorption. In particular, it relates to treatment of disorders which are associated with accelerated loss of bone mass and decreased calcium of bone. These disorders may result in, e.g., decreased bone strength which in turn leads to fracture, pain, and disability, and increased calcium levels in blood, which may be life threatening.

The method involves the application of metal containing compounds, which are useful for treatment of the described disorders.

PRIOR ART

Since the initial date of this application, applicants' copending U.S. application which discloses and claims methods of preventing excessive loss of calcium from human bone by administration of pharmaceutically acceptable gallium metal compounds has issued as U.S. Pat. No. 4,529,593, July 16, 1985. Warrell, et al., *J. Clin. Invest.* 73:1487–1490 (May 1984), disclose the effect of gallium nitrate on calcium resorption in patients with cancer-related hypercalcemia. Warrell, et al., *Cancer* 51:1982–1987 (June 1983), and Leyland-Jones, et al., in *Cancer Treatment Reports* 67, No. 10, 941–942 (Oct. 1983), disclose a safe and non-toxic means for administration of gallium nitrate by continuous infusion.

The applicants' original work with gallium-containing compounds has been expanded to evaluate the effects of other metal-containing compounds upon bone resorption. Various metal-containing compounds have been safely used as medicinals for many years (for review see Metal Toxicity in Mammals, vols. 1 & 2, Volgupal and Luckey, Plenum Press: New York, 1978). However, there is no disclosure in the prior art that any metal-based compound other than gallium could be specifically employed for treatment of bone resorptive disorders. Platinum-containing drugs have been used as anticancer drugs, and the use of platinum is known to induce a variety of metabolic abnormalities in blood, including reduced calcium and magnesium concentrations (see Blachley and Hill, *Annals of Internal Medicine* 95:628–632, 1981). Kukla, et al., (*Clinical Research* 31:739, Oct. 1983) observed that injections of cisplatin (cisdiamminedichloroplatium-II) into mice with hig blood levels of calcium reduced the degree of calcium elevation. However, they did not show that this effect occurred independent from the previously reported effects of cisplatin on blood calcium which may be due to kidney toxicity.

There is no disclosure or suggestion in the prior art that pharmacologically effective amounts of pharmaceutically acceptable metal-containing compounds directly decrease bone resorption.

BACKGROUND

Bone tissue contains high concentrations of calcium, usually in the form of crystalline hydroxyapatite, i.e. $Ca_{10}(PO_4)_6(OH)_2$. Hydroxyapatite—and the calcium of the bone—exist in equilibrium with body fluids, particularly blood. Although the calcium and hydroxyapatite are soluble in blood, the equilibrium is maintained in healthy individuals, along with a stable and intact bone matrix. Since bone is living tissue, it is constantly being remodeled. Certain bone cells, known as osteoblasts, promote bone formation. Other bone cells, known as osteoclasts, tend to cause bone dissolution. The biological process of calcification is critical in providing the mechanical strength for the skeleton and teeth. Pathological states associated with accelerated bone resorption and loss of bone mineral lead to disease characterized by skeletal dysfunction and life-threatening metabolic disorders.

Loss of bone mass from increased bone resorption results in accelerated loss of calcium into the blood. Accelerated bone loss is a major cause of illness in the United States which affects millions of individuals. When significant depletion of bone calcium occurs and the structural integrity of the skeleton is compromised, several diseases result. An example of a disease state associated with severe loss of bone mass is osteoporosis, a major cause of hip and vertebral fractures in older women. Hypercalcemia, or increased blood calcium concentration, occurs frequently in patients who suffer from hyperparathyroidism or cancer. This bone resorptive disorder can lead to kidney failure, coma, and death. Bone metastasis, or the spread of cancer cells into bone, occurs in many patients with cancer and causes progressive bone erosion, fractures, and pain. All of these conditions would be ameliorated by drugs which decrease bone resorption and potentially increase bone tissue calcium content.

Clearly, then, there has been a long-standing need for a treatment which would prevent resorption of calcium from bone. Further, by affecting the balance between resorption and new bone formation, one would also expect that such drugs would increase the rate of calcium accretion in bone.

It has been found that compounds containing the metal gallium, and gallium nitrate in particular, are effective in reducing excessive loss of bone calcium in humans. This method has been disclosed and patented by applicants' U.S. Pat. No. 4,529,593 (7/16/85) the disclosure of which is incorporated by reference. There was no teaching until the present, however that other metal-containing compounds could also decrease bone resorption.

Other metal-containing compounds, so defined by virtue of their relative position in the Periodic Table of the Elements, and their elemental electropositivity, malleability, and conductivity, also interact with bone cells or with the crystalline bone matrix and thereby favorably alter the balance between bone formation and resorption. This supposition has been proven by experiments disclosed herein.

It has been found that metal-containing compounds act on bone tissue to decrease the rate of calcium loss when resorption is stimulated. These metallic compounds retard the destruction of preexisting bone tissue (so called "osteolysis") as a result of various disorders (e.g., metastasis of cancer tumors; hypercalcemia caused by cancer; parathyroid hormone or lymphokine-related compounds; osteoporosis, periodontal disease; or increased bone cell resorbing activity). The metallic compounds used have a low order of toxicity and are pharmaceutically acceptable. They are administered in sufficient dosages to be effective. The effective amount and route of administration (e.g., intravenous, oral, topical, etc.) of the particular compound will vary based upon the nature of the disease being treated, its severity, the age of the patient, and other factors which will be apparent to one skilled in the art.

The following particulars of the invention describe preferred aspects thereof. These particulars, however, should not be taken as limitations to the invention as described, but only of examples of particular, preferred embodiments.

DETAILED DESCRIPTION OF THE PREFERRED EMBODIMENTS

Based on the teaching that gallium—an earth metal of the Group IIIa elements—was found to inhibit calcium loss from bone, the effects of various other metal compounds were evaluated for their ability to inhibit bone resorption. An in vitro assay system was used to examine the activity of these metal compounds. The following experiments were designed to determine if administration of metallic compounds can prevent bone resorption.

Pregnant adult rats were injected with 0.2–0.4 mCi of $^{45}CaCl_2$ on the 18th day of gestation. After 2 days of bone mineralization in utero, the $^{45}Ca$-labeled radii and ulnae of the fetal rats were removed and the bone explants were placed on stainless steel rafts in culture media. Calcium release from bone was stimulated by the addition of highly purified, human 1-34 parathyroid hormone (PTH) or a lymphokine preparation (known to contain osteoclast activating factors). The various metals that were tested were added to the culture media simultaneously with—or 18 to 48 hours prior to—the addition of the bone resorbing factors. After exposure to lymphokine or PTH, the amount of calcium released from the explanted bones was determined by counting the supernatant media in a liquid scintillation counter. Data are expressed as the radio of calcium release in counts per minute (cpm) of the experimental bone treated with a metal and a resorbing factor) to cpm release by a paired control cone (i.e., cpm experimental/cpm control=E/C). Alternatively, the percent change from control due to the addition of metal is reported to illustrate the degree to which resorption was inhibited.

In Table 1, the dose-dependent ability of parathyroid hormone (PTH) to cause calcium release from the fetal rat bones is summarized. PTH is a hormone produced by the parathyroid glands and is responsible for maintaining serum calcium levels largely by inducing calcium release from bone. The data in Table 1 and the subsequent experiments were obtained using the highly purified, biological active 1-34 amino acid fragment of human PTH.

TABLE 1

| Effect of Parathyroid Hormone on $^{45}Ca$ Release | |
|---|---|
| PTH (uM) | E/C |
| 0 | 1.00 ± 0.04 |
| 0.001 | 1.13 ± 0.05 |
| 0.010 | 1.85 ± 0.05 |
| 0.10 | 2.37 ± 0.11 |

These data confirm that PTH causes release of $^{45}Ca$ from fetal rat bones at physiologically relevant levels and in a dose dependent manner.

In Table 2, the effect of three salts of gallium metal are compared. Bone resorption in these experiments was induced by purified human PTH. In each case, bone resorption (i.e., calcium release) in the non-gallium treated bones was increased more than 100% by PTH. In all cases, significant inhibition of calcium loss from bone resulted when gallium concentrations of 2.5 $\mu M$ and greater were tested.

TABLE 2

| Effects of Gallium Compounds on PTH-Stimulated Bone Resorption | | | |
|---|---|---|---|
| Gallium Concentration | Gallium Nitrate | Gallium Acetate | Gallium Fluoride |
| 0 | 2.25 ± 0.43[1] | 3.10 ± 0.2 | 2.56 ± 0.29 |
| 2.25 uM | 2.19 ± 0.64 | 2.55 ± 0.26 | 1.80 ± 0.26 |
| 12.5 uM | 1.35 ± 0.07 | 1.63 ± 0.06 | 0.91 ± 0.03 |

[1] Mean [E/C = CPM $^{45}Ca$ release from experimental bones/CPM $^{45}Ca$ release from control bones] ± SEM, n = 4.

These data also document that it is the elemental metal which is critical in order to effect bone resorption. The other elements to which the metal is complexed (in this case, the ionic components of nitrate, acetate, and fluoride) are not material to this activity. These components are relevant only insofar as they affect pharmaceutical acceptability of the compound.

In Table 3, the ability of other metal compounds to block bone resorption was tested, via the methods described supra. In each case, these metal compounds effectively prevented the loss of calcium from bone at concentrations that were comparable to gallium.

TABLE 3

| Effects of Various Metal Compounds on Bone Resorption | | | |
|---|---|---|---|
| Metal | Compound | Concentration (uM) | % Inhibition of PTH-Induced Resorption |
| Ga | gallium nitrate | 2.5 | 5 |
|  |  | 12.5 | 72 |
| Pt | cis-diammine dichloroplatinum II | 3.3 | 34 |
|  |  | 6.7 | 80 |
|  |  | 16.7 | 100 |
| Pt | cis-diammine 1,1,-cyclobutane dicarboxylate platinum II (carboplatin) | 25.0 | 12 |
|  |  | 37.5 | 35 |
|  |  | 62.0 | 100 |
| Ge | Spirogermanium | 2.5 | 0 |
|  |  | 5.0 | 51 |
|  |  | 12.5 | 100 |

From these data, one concludes that these metal compounds were capable of preventing bone calcium release (i.e., accelerated bone resorption) at pharmacologically achievable concentrations. One skilled in the art will immediately see the applicability of these preferred embodiments to other compounds and situations. For example, gallium, platinum, and germanium all share properties common to metals. Hence, one skilled in the art would expect that other metal compounds, chemically defined because of their lustre, malleability, conductivity, electropositivity, and relative position in the Periodic Table of the Element would also be effective in decreasing resorption of calcium from the crystalline matrix of bone. These metals would include those elements assigned to groups known as the earth, rare earth, noble, alkali, and basic metals. These elements include metals numbers 13–71 of the periodic table and those with atomic weights ranging from 26–174. Most particularly, these metals include elements of the Groups Ib, IIIa (of which gallium is a member), IIIb, IVa (of which germanium is a member), IVb, Va, Vb, VIa, VIb, VIIa, VIIb, and VIII (of which platinum is a member).

Additionally one would expect the composition and methods described herein to be applicable to similar tissues. Human bone is similar in many respects to bone of other animals. Hence the veterinary applications of this invention are clear. Similarly, the calcium in bones surrounding teeth makes it clear that this invention is applicable to treatment of periodontal disease.

The link between a decrease in bone resorption and a resulting increase in bone strength has been attested to, and one skilled in the art will therefore see that the compositions and methods disclosed herein may be used to increase bone strength.

In the practice of this invention, any of the standard ways of administering compositions to patients may be employed including, but not limited to, concentrated rinses, gels, topical application, intravenous injection, including continuous infusion, oral, sublingual, rectal, or transdermal administration. In a preferred form of the invention using cisdiamminedichloroplatinum II (cisplatin), intravenous, intramuscular, or subcutaneous injection supplies about 1-120 mg/sq m/day to patients. Preferred embodiments of carboplatin by injection supplies 1-450 mg/sq m/day to patients and even more preferably, 3-100 mg/sq m/day. A preferred embodiment of germanium, used as spirogermanium, supplies about 0.5 to 100 mg/sq m/day to patients when administered by injection. When administered orally, sublingually, rectally or transdermally, the compounds are administered in higher doses in amounts ranging from about 0.5-20 grams/day. It is recognized that these preferred embodiments are provided only as examples and that one skilled in the art could refer to other metal-containing compounds as having effective activities on bone resorption administered in pharmaceutically acceptable amounts. It is further recognized that the chemical entity to which the metal is bound or complexed (e.g., an anion) is not material to the anti-resorptive action but is relevant only to the extent that it may improve its pharmaceutical acceptability (e.g., reduced toxicity, increased bioavailability, improved stability in solution, etc.).

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method of decreasing bone resorption comprising administering to a subject with a bone resorptive disorder a pharmaceutically acceptable composition containing a germanium or platinum containing compound useful in decreasing bone resorption in an amount sufficient to cause bone resorption.

2. A method as in claim 1, wherein said disease is periodontal disease.

3. A method as in claim 1, wherein said disease is cancer related.

4. A method as in claim 1, wherein said disease is hypercalcemia.

5. A method as in claim 1, wherein said disease is osteoporosis.

6. A method as in claim 1, wherein said disease is caused by a parathyroid hormone, a cytokine, or other bone-resorbing factor lymphokine related compound.

7. A method as in claim 1, wherein said disease is malignant bone metastases.

8. A method as in claim 1, wherein said disease is Paget's disease.

9. A method as in claim 1, wherein said disease is an inflammatory disorder of bones or joints.

10. A method as in claim 1, wherein said subject is a human.

11. A method as in claim 1, wherein said subject is a veterinary subject.

12. A method as in claim 1, wherein said compound is administered intra-orally in a topical formulation comprising a concentrated rinse, gel, or other pharmaceutically acceptable carrier.

13. A method as in claim 1, wherein said compound is administered intravenously, subcutaneously, or intramuscularly.

14. A method as in claim 1, wherein said compound is administered by continuous intravenous infusion.

15. A method of claim 1, wherein said compound is administered by intravenous injection comprising an amount ranging from about 1-450 mg/sq m/day.

16. A method as in claim 1, wherein said compound is administered orally, topically, sublingually, per rectum or transdermally.

17. A method as in claim 1, wherein said compound is administered orally, topically, sublingually, per rectum or transdermally in an amount ranging from about 0.5-20 grams/day.

18. A method as in claim 1, wherein said compound is a platinum containing compound.

19. A method as in claim 1, wherein said compound is a germanium containing compound.

20. A method as in claim 18, wherein said compound is cis-diammine dichloro-platinum II.

21. A method as in claim 18, wherein said compound cis-diammine 1,1-cyclobutane dicarboxylate platinum II.

22. A method as in claim 19, wherein said compound is spirogermanium.

23. A method as in claim 20, wherein said compound is administered by intravenous, intramuscular, or subcutaneous injection.

24. A method as in claim 20, wherein said compound is administered in an amount ranging from about 1 to about 120 mg/sq m/day.

25. A method as in claim 21, wherein said compound is administered by intravenous, intramuscular, or subcutaneous injection.

26. A method as in claim 21, wherein said compound is administered in an amount ranging from about 1 to about 450 mg/sq m/day.

27. A method as in claim 21, wherein said compound is administered in an amount ranging from about 3 to about 100 mg/sq m/day.

28. A method as in claim 22, wherein said compound is administered by intravenous, intramuscular, or subcutaneous injection.

29. A method as in claim 22, wherein said compound is administered in an amount ranging from about 0.5 to about 100 mg/sq m/day.

30. A method as in claims 22 or 24, wherein said compound is administered orally, sublingually, rectally, or transdermally.

31. A method as in claim 22, wherein said compound is administered in an amount ranging from about 0.5 to about 20 grams/day.

* * * * *